US006333161B1

(12) United States Patent
Kamboj et al.

(10) Patent No.: US 6,333,161 B1
(45) Date of Patent: Dec. 25, 2001

(54) KAINATE-BINDING, HUMAN CNS RECEPTORS OF THE EAA5 FAMILY

(75) Inventors: Rajender Kamboj, Mississauga; Candace E. Elliott; Stephen L. Nutt, both of Etobicoke, all of (CA)

(73) Assignee: NPS Allelix Corporation, Mississauga (CA)

( * ) Notice: Subject to any disclaimer, the term of this patent is extended or adjusted under 35 U.S.C. 154(b) by 0 days.

(21) Appl. No.: 08/178,019

(22) Filed: Jan. 6, 1994

Related U.S. Application Data

(62) Division of application No. 07/945,210, filed on Sep. 17, 1992, now abandoned.

(51) Int. Cl.$^7$ ............................ C12N 15/63; C12N 15/85; C12N 15/09
(52) U.S. Cl. ........................... 435/7.1; 435/69.1; 536/23.5
(58) Field of Search .............................. 435/69.1, 240.1, 435/7.1; 530/395, 350; 536/23.5

(56) References Cited

FOREIGN PATENT DOCUMENTS

| WO 91/06648 | 5/1991 | (WO) . |
| WO 92/10583 | 6/1992 | (WO) . |

OTHER PUBLICATIONS

Egebjerg, et al., "Cloning of a cDNA for a Glutamate Receptor Subunit Activated by Kainate but not AMPA", Nature, vol. 351, Jun., 1991, pp. 745–748.
Bettler, et al., "Cloning of a Putative Glumate Receptor: A Low Affinity Kainate–Binding Subunit", Neuron, vol. 8, Feb., 1992, pp. 257–265.
Wada, et al., "Sequence and Expression of a Frog Brain Complementary DNA Encoding a Kainate–Binding Protein", Nature, vol. 342, Dec., 1989, pp. 684–689.
Gegor, et al., "Molecular Structure of the Chick Cerebellar Kainate–Binding Subunit of a Putative Glutamate Receptor", Nature, vol. 342, Dec., 1989, pp. 689–692.
Werner, et al., "Cloning of a Putative High–Affinity Kainate Receptor in Hippocampal CA3 Cells", Nature, vol. 351, Jun., 1991, pp. 742–744.
Bettler, et al., "Cloning of a Novel Glutamate Receptor Subunit, GluR5: Expression in the Nervous System During Development", Neuron, vol. 5, Nov., 1990, pp. 583–595.
Kozak, et al., "An Analysis of 5'–Noncoding Sequences from 699 Vertebrate Messenger RNAs", Nucleic Acids Research, vol. 15, No. 20, 1987, pp. 8125–8132.
Verdoom, et al., "Excitatory Amino Acid Receptors Expressed in Xenopus Oocytes: Agonist Pharmacology", Molecular Pharmacology, vol. 34, Jun., 1988, pp. 298–307.
Hollmann, et al., "Cloning by Functional Expression of a Member of the Glumate Receptor Family", Nature, vol. 342, Dec., 1989, pp. 643–648.

Keinanen, et al., "A Family of AMPA–Selective Glutamate Receptors", Science, vol. 249, Aug., 1990, pp. 556–560.
Boulter, et al., "Molecular Cloning and Functional Expression of Glutamate Receptor Subunit Genes", Science, vol. 249, Aug., 1990, pp. 1033–1037.
Sommer, et al., "Flip and Flop: A Cell–Specific Functional Switch in Glumtamate–Operated Channels of the CNS", Science, vol. 249, Aug., 1990, pp. 1580–1585.
Monyer, et al., "Glutamate–Operated Channels: Developmentally Early and Mature Forms Arise by Alternative Splicing", Neuron, vol. 6, May, 1991, pp. 799–810.
Nakanishi, et al., "A Family of Glutamate Receptor Genes: Evidence for the Formation of Heteromultimeric Receptors with Distinct Channel Properties", Neuron, vol. 5, Nov., 1990, pp. 569–581.
Hollmann, et al., "Ca2 + Permeability of KA–AMPA–Gated Glutamate Receptor Channels Depends on Subunit Composition", Science, vol. 252, May, 1991, pp. 851–853.
Verdoom, et al., "Structural Determinants of Ion Flow Through Recombinant Glutamate Receptor Channels", vol. 252, Jun., 1991, pp. 1715–1718.
Coffer et al., 1990, FEBS, 274, 159–164.
Sommer et al., 1992, Embo J., 11, 1651–1656.
William Sun, et al., "Molecular cloning, chromosomal mapping, and functional expression of human brain glutamate receptors", Proc. Natl. Acad. Sci. USA, vol. 89, pp. 1443–1447, Feb. 1992.
Carmie Puckett, et al., "Molecular cloning and chromosomal localization of one of the human glutamate receptor genes"; Proc. Natl. Acad. Sci. USA, vol. 88, pp. 7557–7561, Sep. 1991.

*Primary Examiner*—Gary L. Kunz
(74) *Attorney, Agent, or Firm*—Foley & Lardner

(57) ABSTRACT

Neurotransmission by excitatory amino acids (EAAs) such as glutamate is mediated via membrane-bound surface receptors. DNA coding for one family of these receptors of the kainate-binding type of EAA receptors, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

3 Claims, 16 Drawing Sheets

FIG. 1A

```
     HindIII
        |
        |
        AAGCTTGCCGCCACCATGACCGCTCCCTGGCGGCGCCTCCGGAGTCTGGTTTGGGAATAC
  1     ----------+----------+----------+----------+----------+----------+ 60
        TTCGAACGGCGGTGGTACTGGCGAGGGACCGCCGCGGAGGCCTCAGACCAAACCCTTATG

-31 M  T  A  P  W  R  R  L  R  S  L  V  W  E  Y   -17

TGGGCCGGGCTCCTCGTGTGCGCCTTCTGGATCCCGGACTCGCGCGGGATGCCCCACGTC
 61     ----------+----------+----------+----------+----------+----------+ 120
        ACCCGGCCCGAGGAGCACACGCGGAAGACCTAGGGCCTGAGCGCGCCCTACGGGGTGCAG

W  A  G  L  L  V  C  A  F  W  I  P  D  S  R  G  M  P  H  V    4
                                                           |
                                                           |_Mature N-Terminal ATCCGGATCGGAGGAATCTTCGAGTATGCGGACGGCCCCAACGCCCAGGTCATGAATGCC
121     ----------+----------+----------+----------+----------+----------+ 180
        TAGGCCTAGCCTCCTTAGAAGCTCATACGCCTGCCGGGGTTGCGGGTCCAGTACTTACGG

I  R  I  G  G  I  F  E  Y  A  D  G  P  N  A  Q  V  M  N  A   24

GAGGAGCATGCCTTTCGATTTTCTGCCAACATCATCAACAGGAACAGGACTCTGCTGCCC
181     ----------+----------+----------+----------+----------+----------+ 240
        CTCCTCGTACGGAAAGCTAAAAGACGGTTGTAGTAGTTGTCCTTGTCCTGAGACGACGGG

E  E  H  A  F  R  F  S  A  N  I  I  N  R  N  R  T  L  L  P   44

AACACAACCTTGACCTATGACATACAGAGGATTCACTTCCATGACAGCTTCGAGGCGACC
241     ----------+----------+----------+----------+----------+----------+ 300
        TTGTGTTGGAACTGGATACTGTATGTCTCCTAAGTGAAGGTACTGTCGAAGCTCCGCTGG
```

AAAAAGGCCTGTGACCAGCTGGCACTGGGCGTGGTGGCGATCTTCGGCCCATCACAGGGC
301   ----------+---------+---------+---------+---------+---------+      360
      TTTTTCCGGACACTGGTCGACCGTGACCCGCACCACCGCTAGAAGCCGGGTAGTGTCCCG

K  K  A  C  D  Q  L  A  L  G  V  V  A  I  F  G  P  S  Q  G        84

TCCTGCACCAATGCCGTCCAGTCCATCTGCAATGCCCTGGAGGTGCCCCACATCCAGCTG
361   ----------+---------+---------+---------+---------+---------+      420
      AGGACGTGGTTACGGCAGGTCAGGTAGACGTTACGGGACCTCCACGGGGTGTAGGTCGAC

S  C  T  N  A  V  Q  S  I  C  N  A  L  E  V  P  H  I  Q  L       104

CGTTGGAAGCACCACCCGCTGGACAACAAGGACACCTTCTACGTGAACCTCTACCCCGAC
421   ----------+---------+---------+---------+---------+---------+      480
      GCAACCTTCGTGGTGGGCGACCTGTTGTTCCTGTGGAAGATGCACTTGGAGATGGGGCTG

R  W  K  H  H  P  L  D  N  K  D  T  F  Y  V  N  L  Y  P  D       124

TACGCCTCGCTCAGCCATGCCATCCTCGACCTGGTCCAGTACCTCAAGTGGCGGTCGGCC
481   ----------+---------+---------+---------+---------+---------+      540
      ATGCGGAGCGAGTCGGTACGGTAGGAGCTGGACCAGGTCATGGAGTTCACCGCCAGCCGG

```
    ACCGTGGTCTATGACGACAGTACAGGGCTCATCCGACTGCAGGAGCTCATCATGGCCCCA
541 ------------+----------+----------+----------+----------+---------+ 600
    TGGCACCAGATACTGCTGTCATGTCCCGAGTAGGCTGACGTCCTCGAGTAGTACCGGGGT

T  V  V  Y  D  D  S  T  G  L  I  R  L  Q  E  L  I  M  A  P    164

TCAAGATACAACATCCGCCTGAAGATCCGTCAGCTCCCCATCGACTCTGACGACTCGCGC
601 ------------+----------+----------+----------+----------+---------+ 660
    AGTTCTATGTTGTAGGCGGACTTCTAGGCAGTCGAGGGGTAGCTGAGACTGCTGAGCGCG

S  R  Y  N  I  R  L  K  I  R  Q  L  P  I  D  S  D  D  S  R    184

EcoRI
                                            |
    CCCTTGCTCAAGGAGATGAAGCGAGGCCGGGAATTCCGCATTATCTTCGACTGCAGCCAC
661 ------------+----------+----------+----------+----------+---------+ 720
    GGGAACGAGTTCCTCTACTTCGCTCCGGCCCTTAAGGCGTAATAGAAGCTGACGTCGGTG

P  L  L  K  E  M  K  R  G  R  E  F  R  I  I  F  D  C  S  H    204

ACTATGGCGGCCCAGATCCTCAAGCAGGCCATGGCCATGGGCATGATGACTGAGTACTAC
721 ------------+----------+----------+----------+----------+---------+ 780
    TGATACCGCCGGGTCTAGGAGTTCGTCCGGTACCGGTACCCGTACTACTGACTCATGATG

T  M  A  A  Q  I  L  K  Q  A  M  A  M  G  M  M  T  E  Y  Y    224

CACTTCATCTTCACCACTCTGGATCTCTACGCTTTAGACCTGGAGCCCTACCGCTACTCA
781 ------------+----------+----------+----------+----------+---------+ 840
    GTGAAGTAGAAGTGGTGAGACCTAGAGATGCGAAATCTGGACCTCGGGATGGCGATGAGT

```
     GGCGTGAACCTGACAGGATTCCGGATTCTCAATGTGGACAACCCACACGTCTCGGCCATT
841  ----------+---------+---------+---------+---------+---------+ 900
     CCGCACTTGGACTGTCCTAAGGCCTAAGAGTTACACCTGTTGGGTGTGCAGAGCCGGTAA

G  V  N  L  T  G  F  R  I  L  N  V  D  N  P  H  V  S  A  I    264

GTGGAGAAGTGGTCCATGGAGCGGCTGCAGGCAGCTCCCCGGGCCGAGTCTGGCCTGCTG
901  ----------+---------+---------+---------+---------+---------+ 960
     CACCTCTTCACCAGGTACCTCGCCGACGTCCGTCGAGGGGCCCGGCTCAGACCGGACGAC

V  E  K  W  S  M  E  R  L  Q  A  A  P  R  A  E  S  G  L  L    284

GATGGAGTAATGATGACTGATGCAGCCTTACTGTACGACGCCGTCCATATCGTGTCCGTG
961  ----------+---------+---------+---------+---------+---------+ 1020
     CTACCTCATTACTACTGACTACGTCGGAATGACATGCTGCGGCAGGTATAGCACAGGCAC

D  G  V  M  M  T  D  A  A  L  L  Y  D  A  V  H  I  V  S  V    304

TGCTACCAGCGGGCACCACAGATGACCGTGAACTCCCTGCAGTGCCATCAGCACAAGGCC
1021 ----------+---------+---------+---------+---------+---------+ 1080
     ACGATGGTCGCCCGTGGTGTCTACTGGCACTTGAGGGACGTCACGGTAGTCGTGTTCCGG

C  Y  Q  R  A  P  Q  M  T  V  N  S  L  Q  C  H  Q  H  K  A    324

NotI
                     |
     TGGCGCTTTGGCGGCCGCTTCATGAACTTCATCAAGGAGGCTCAATGGGAAGGATTAACT
1081 ----------+---------+---------+---------+---------+---------+ 1140
     ACCGCGAAACCGCCGGCGAAGTACTTGAAGTAGTTCCTCCGAGTTACCCTTCCTAATTGA

```
     GGACGAATTGTTTTCAACAAAACTAGTGGCTTGCGGACGGATTTTGATCTGGACATCATC
1141 ------------+----------+----------+----------+----------+----------+ 1200
     CCTGCTTAACAAAAGTTGTTTTGATCACCGAACGCCTGCCTAAAACTAGACCTGTAGTAG

G   R   I   V   F   N   K   T   S   G   L   R   T   D   F   D   L   D   I   I    364

AGCCTGAAAGAGGATGGCCTGGAGAAGGTTGGGGTGTGGAGTCCTGCCGACGGGCTCAAC
1201 ------------+----------+----------+----------+----------+----------+ 1260
     TCGGACTTTCTCCTACCGGACCTCTTCCAACCCCACACCTCAGGACGGCTGCCCGAGTTG

S   L   K   E   D   G   L   E   K   V   G   V   W   S   P   A   D   G   L   N    384

ATCACTGAGGTTGCCAAAGGCCGAGGCCCTAATGTCACCGACTCTCTGACAAACAGATCA
1261 ------------+----------+----------+----------+----------+----------+ 1320
     TAGTGACTCCAACGGTTTCCGGCTCCGGGATTACAGTGGCTGAGAGACTGTTTGTCTAGT

I   T   E   V   A   K   G   R   G   P   N   V   T   D   S   L   T   N   R   S    404

CTCATTGTCACCACAGTGCTGGAGGAGCCCTTCGTCATGTTTCGGAAATCAGACAGGACG
1321 ------------+----------+----------+----------+----------+----------+ 1380
     GAGTAACAGTGGTGTCACGACCTCCTCGGGAAGCAGTACAAAGCCTTTAGTCTGTCCTGC

L   I   V   T   T   V   L   E   E   P   F   V   M   F   R   K   S   D   R   T    424

CTATATGGGAATGACCGGTTCGAGGGCTACTGCATCGACCTGCTAAAGGAGCTGGCCCAC
1381 ------------+----------+----------+----------+----------+----------+ 1440
     GATATACCCTTACTGGCCAAGCTCCCGATGACGTAGCTGGACGATTTCCTCGACCGGGTG

```
      ATCCTTGGTTTCTCCTATGAGATCCGGCTGGTGGAGGACGGCAAGTACGGGGCACAGGAT
1441  ------------+---------+---------+---------+---------+---------+ 1500
      TAGGAACCAAAGAGGATACTCTAGGCCGACCACCTCCTGCCGTTCATGCCCCGTGTCCTA

I  L  G  F  S  Y  E  I  R  L  V  E  D  G  K  Y  G  A  Q  D    464

GACAAGGGCCAGTGGAACGGCATGGTCAAGGAGCTCATCGACCACAAGGCAGATCTGGCC
1501  ------------+---------+---------+---------+---------+---------+ 1560
      CTGTTCCCGGTCACCTTGCCGTACCAGTTCCTCGAGTAGCTGGTGTTCCGTCTAGACCGG

D  K  G  Q  W  N  G  M  V  K  E  L  I  D  H  K  A  D  L  A    484

GTGGCCCCCCTGACCATCACCCATGTTCGAGAGAAGGCCATCGACTTCTCCAAGCCCTTC
1561  ------------+---------+---------+---------+---------+---------+ 1620
      CACCGGGGGGACTGGTAGTGGGTACAAGCTCTCTTCCGGTAGCTGAAGAGGTTCGGGAAG

V  A  P  L  T  I  T  H  V  R  E  K  A  I  D  F  S  K  P  F    504

ATGACACTTGGTGTGAGCATCCTGTATCGAAAGCCCAATGGCACCAACCCCAGCGTCTTC
1621  ------------+---------+---------+---------+---------+---------+ 1680
      TACTGTGAACCACACTCGTAGGACATAGCTTTCGGGTTACCGTGGTTGGGGTCGCAGAAG

M  T  L  G  V  S  I  L  Y  R  K  P  N  G  T  N  P  S  V  F    524

TCCTTCCTCAATCCCCTGTCCCCAGACATCTGGATGTATGTTCTCCTCGCCTACCTGGGG
1681  ------------+---------+---------+---------+---------+---------+ 1740
      AGGAAGGAGTTAGGGGACAGGGGTCTGTAGACCTACATACAAGAGGAGCGGATGGACCCC

```
     GTCAGCTGTGTCCTCTTCGTCATCGCCAGGTTCAGCCCTTATGAGTGGTACGATGCTCAC
1741 ----------+----------+----------+----------+----------+----------+ 1800
     CAGTCGACACAGGAGAAGCAGTAGCGGTCCAAGTCGGGAATACTCACCATGCTACGAGTG

V  S  C  V  L  F  V  I  A  R  F  S  P  Y  E  W  Y  D  A  H    564

CCCTGCAACCCTGGCTCCGAGGTGGTGGAAAATAACTTCACTCTGCTTAACAGCTTCTGG
1801 ----------+----------+----------+----------+----------+----------+ 1860
     GGGACGTTGGGACCGAGGCTCCACCACCTTTTATTGAAGTGAGACGAATTGTCGAAGACC

P  C  N  P  G  S  E  V  V  E  N  N  F  T  L  L  N  S  F  W    584

TTTGGAATGGGATCCCTGATGCAGCAAGGGTCTGTGCTGATGCCCAAAGCCCTGTCCACA
1861 ----------+----------+----------+----------+----------+----------+ 1920
     AAACCTTACCCTAGGGACTACGTCGTTCCCAGACACGACTACGGGTTTCGGGACAGGTGT

F  G  M  G  S  L  M  Q  Q  G  S  V  L  M  P  K  A  L  S  T    604

CGCATCATTGGTGGCATCTGGTGGTTCTTTACGCTCATCATCATCTCTTCCTACACGGCC
1921 ----------+----------+----------+----------+----------+----------+ 1980
     GCGTAGTAACCACCGTAGACCACCAAGAAATGCGAGTAGTAGTAGAGAAGGATGTGCCGG

R  I  I  G  G  I  W  W  F  F  T  L  I  I  I  S  S  Y  T  A    624

AACCTGGCTGCCTTTCTGACCGTGGAGCGCATGGAATCACCCATTGACTCTGCTGATGAC
1981 ----------+----------+----------+----------+----------+----------+ 2040
     TTGGACCGACGGAAAGACTGGCACCTCGCGTACCTTAGTGGGTAACTGAGACGACTACTG

```
     CTGGCCAAGCAAACCAAAATCGAGTATGGGGCTGTCAAGGATGGGGCCACCATGACCTTC
2041 ----------+----------+----------+----------+----------+----------+ 2100
     GACCGGTTCGTTTGGTTTTAGCTCATACCCCGACAGTTCCTACCCCGGTGGTACTGGAAG

L  A  K  Q  T  K  I  E  Y  G  A  V  K  D  G  A  T  M  T  F    664

TTCAAGAAATCCAAGATCTCCACCTTCGAGAAGATGTGGGCCTTCATGAGCAGGAAGCCA
2101 ----------+----------+----------+----------+----------+----------+ 2160
     AAGTTCTTTAGGTTCTAGAGGTGGAAGCTCTTCTACACCCGGAAGTACTCGTCCTTCGGT

F  K  K  S  K  I  S  T  F  E  K  M  W  A  F  M  S  R  K  P    684

TCGGCGCTGGTGAAGAACAACGAGGAGGGCATCCAGAGGGCCCTGACGGCCGACTACGCG
2161 ----------+----------+----------+----------+----------+----------+ 2220
     AGCCGCGACCACTTCTTGTTGCTCCTCCCGTAGGTCTCCCGGGACTGCCGGCTGATGCGC

S  A  L  V  K  N  N  E  E  G  I  Q  R  A  L  T  A  D  Y  A    704

CTGCTCATGGAGTCCACCACCATCGAGTACGTCACGCAGAGGAACTGCAACCTCACCCAG
2221 ----------+----------+----------+----------+----------+----------+ 2280
     GACGAGTACCTCAGGTGGTGGTAGCTCATGCAGTGCGTCTCCTTGACGTTGGAGTGGGTC

L  L  M  E  S  T  T  I  E  Y  V  T  Q  R  N  C  N  L  T  Q    724

ATCGGGGGCCTCATTGACTCCAAGGGCTACGGCATCGGCACGCCCATGGGCTCCCCATAC
2281 ----------+----------+----------+----------+----------+----------+ 2340
     TAGCCCCCGGAGTAACTGAGGTTCCCGATGCCGTAGCCGTGCGGGTACCCGAGGGGTATG

```
      CGGGACAAGATCACCATCGCCATCCTGCAGCTTCAGGAGGAGGACAAGCTGCATATCATG
2341  ---------+---------+---------+---------+---------+---------+ 2400
      GCCCTGTTCTAGTGGTAGCGGTAGGACGTCGAAGTCCTCCTCCTGTTCGACGTATAGTAC

R  D  K  I  T  I  A  I  L  Q  L  Q  E  E  D  K  L  H  I  M    764

AAGGAGAAGTGGTGGCGGGGCAGCGGGTGTCCTGAGGAGGAAAACAAAGAGGCCAGTGCC
2401  ---------+---------+---------+---------+---------+---------+ 2460
      TTCCTCTTCACCACCGCCCCGTCGCCCACAGGACTCCTCCTTTTGTTTCTCCGGTCACGG

K  E  K  W  R  G  S  G  C  P  E  E  E  N  K  E  A  S  A       784

CTGGGGATCCAGAAGATCGGGGGCATCTTCATTGTCCTGGCCGCCGGGCTGGTCCTCTCT
2461  ---------+---------+---------+---------+---------+---------+ 2520
      GACCCCTAGGTCTTCTAGCCCCCGTAGAAGTAACAGGACCGGCGGCCCGACCAGGAGAGA

L  G  I  Q  K  I  G  G  I  F  I  V  L  A  A  G  L  V  L  S    804

GTGCTGGTGGCCGTGGGCGAGTTTGTGTACAAGCTCCGCAAAACAGCAGAGAGAGAGCAG
2521  ---------+---------+---------+---------+---------+---------+ 2580
      CACGACCACCGGCACCCGCTCAAACACATGTTCGAGGCGTTTTGTCGTCTCTCTCTCGTC

V  L  V  A  V  G  E  F  V  Y  K  L  R  K  T  A  E  R  E  Q    824

CGTTCCTTCTGCAGCACCGTGGCCGATGAGATCCGTTTCTCCCTTACCTGCCAGCGTCGA
2581  ---------+---------+---------+---------+---------+---------+ 2640
      GCAAGGAAGACGTCGTGGCACCGGCTACTCTAGGCAAAGAGGGAATGGACGGTCGCAGCT

```
      GTCAAGCACAAGCCTCAGCCTCCCATGATGGTCAAGACTGACGCCGTCATCAACATGCAC
2641  ------------+----------+----------+----------+----------+----------+  2700
      CAGTTCGTGTTCGGAGTCGGAGGGTACTACCAGTTCTGACTGCGGCAGTAGTTGTACGTG

V   K   H   K   P   Q   P   P   M   M   V   K   T   D   A   V   I   N   M   H    864

ACATTCAATGACCGCCGGCTTCCCGGCAAGGACAGCATGGCCTGCAGCACATCCTTAGCC
2701  ------------+----------+----------+----------+----------+----------+  2760
      TGTAAGTTACTGGCGGCCGAAGGGCCGTTCCTGTCGTACCGGACGTCGTGTAGGAATCGG

T   F   N   D   R   R   L   P   G   K   D   S   M   A   C   S   T   S   L   A    884

CCTGTGTTCCCCTAGGCACAACTGGGGTGGGGACCTCAGGCCTGGGGGCTGGGCAGAGGA
2761  ------------+----------+----------+----------+----------+----------+  2820
      GGACACAAGGGGATCCGTGTTGACCCCACCCCTGGAGTCCGGACCCCCGACCCGTCTCCT

P   V   F   P   *   888

AAGCAAAGGAGATTGGAAGGAACGTCCCCTGTACCCGCACTGGGCTTGGGGACCAGAGCT
2821  ------------+----------+----------+----------+----------+----------+  2880
      TTCGTTTCCTCTAACCTTCCTTGCAGGGGACATGGGCGTGACCCGAACCCCTGGTCTCGA

GCCACCTGCCTGTTGGGCCAGGAGCCTCCTGCCCTTACCTGCCAGGAAGCCAGCAGGCTC
2881  ------------+----------+----------+----------+----------+----------+  2940
      CGGTGGACGGACAACCCGGTCCTCGGAGGACGGGAATGGACGGTCCTTCGGTCGTCCGAG

TCAGGCCAGCTGCTTGGGCTTCATCCTCCTCAGATCTTCTGTGGGTTTCTAAAGCTGCCA
2941  ------------+----------+----------+----------+----------+----------+  3000
      AGTCCGGTCGACGAACCCGAAGTAGGAGGAGTCTAGAAGACACCCAAAGATTTCGACGGT
```

FIG. 1K

```
         GCCGAGATAGCCAAGGCCAAAGGAAGCACATGCCTCTCTCAGGCCAAACTCACCTGCCCC
3001     ---------+---------+---------+---------+---------+---------+ 3060
         CGGCTCTATCGGTTCCGGTTTCCTTCGTGTACGGAGAGAGTCCGGTTTGAGTGGACGGGG

TCAACTCTCCTCCAGAGTCAGAAGTTTCTGCCGCAGCCCTGCAGAGGGCACAGAAAATGG
3061     ---------+---------+---------+---------+---------+---------+ 3120
         AGTTGAGAGGAGGTCTCAGTCTTCAAAGACGGCGTCGGGACGTCTCCCGTGTCTTTTACC

AAGACAGCTCTTATATTGCCATTTCTTCCACAAGAGCCCAGGCCTCCTACAGCTTGACCG
3121     ---------+---------+---------+---------+---------+---------+ 3180
         TTCTGTCGAGAATATAACGGTAAAGAAGGTGTTCTCGGGTCCGGAGGATGTCGAACTGGC

TGAGGCCAGAGACACAAGCCTTCGGCGCCTTAAGGATGTTCTAGCATGGCTGCCAATGGG
3181     ---------+---------+---------+---------+---------+---------+ 3240
         ACTCCGGTCTCTGTGTTCGGAAGCCGCGGAATTCCTACAAGATCGTACCGACGGTTACCC

AGCTCATGGTGAGGGATACCCATCCCATATGCCTGGGCAGAAGGAAGACTTCATCCCTCT
3241     ---------+---------+---------+---------+---------+---------+ 3300
         TCGAGTACCACTCCCTATGGGTAGGGTATACGGACCCGTCTTCCTTCTGAAGTAGGGAGA

GGGGCTGTTCACGTGGTCCTAATCTTCTGAACTTGGCGCTGCCCCTGGCAGCCCCTGTTC
3301     ---------+---------+---------+---------+---------+---------+ 3360
         CCCCGACAAGTGCACCAGGATTAGAAGACTTGAACCGCGACGGGGACCGTCGGGGACAAG
```

FIG. 1L

```
     TGGCAGAGTTGAAGACAGAGCTACACAGGGGAAAAGAGGAGTTTGGGGTATGGGAGAGAA
3361 ----------+---------+---------+---------+---------+---------+ 3420
     ACCGTCTCAACTTCTGTCTCGATGTGTCCCCTTTTCTCCTCAAACCCCATACCCTCTCTT

GAGAATGCACAAACAGAGGCCGCCATTTTGGATTCTTATGGACAATGACCCAGTGGTTCC
3421 ----------+---------+---------+---------+---------+---------+ 3480
     CTCTTACGTGTTTGTCTCCGGCGGTAAAACCTAAGAATACCTGTTACTGGGTCACCAAGG

TAATCCTCTAGGAGGTCTCTAAGAATATAAGTGGGGGAGTGGCCACAGAAAATTCTTCTC
3481 ----------+---------+---------+---------+---------+---------+ 3540
     ATTAGGAGATCCTCCAGAGATTCTTATATTCACCCCCTCACCGGTGTCTTTTAAGAAGAG

CACTTTCTAGCCAGAGGAGAGAGGACCCCCTGAATTTCTCACAAAGGATGCCCAAAGATG
3541 ----------+---------+---------+---------+---------+---------+ 3600
     GTGAAAGATCGGTCTCCTCTCTCCTGGGGGACTTAAAGAGTGTTTCCTACGGGTTTCTAC

EcoRI
                      |
     CAGCCGGTATTTGGAATTC
3601 ----------+--------- 3619
     GTCGGCCATAAACCTTAAG
```

FIG. 3A

```
humEAA5a  1051 AACTCCCTGCAGTGCCATCAGCAGCACAAGGCCTGGCGCTTTGCGGCCGCTT 1100
               ||||||||||||||||||||||||||  ||||||||||||||||||||||||
humEAA5b  1051 AACTCCCTGCAGTGCCATCGGCAGCACAAGGCCTGGCGCTTTGCGGCCGCTT 1100

---------------------------------------------------------------- humEAA5a  2568 AGAGAGAGAGCAGCGGTTCCTTCTGCAGCACCGTGGCCGTGGCCGATGAGATCCGTT 2617
               |||||||||||||||||||||||||||||||||||||||||||||||||||||||||
humEAA5c  2568 AGAGAGAGAGCAGCGGTTCCTTCTGCAGCACCGTGGCCGTGGCCGATGAGATCCGTT 2617 humEAA5a  2618 TCTCCCTTACCTGCCAGCGTCGAGTCAAGCACAAGCCTCAGCCTCCCATG 2667
               |||||| |||  |||||    |   ||  ||  ||   ||  ||
humEAA5c  2618 TCTCCCCACCCCTAAACGCAGCCGGCCTACCCCCTGCACAAGCAGGAATTC 2667
```

FIG. 3B

```
humEAA5a   295  LYDAVHIVSVCYQRAPQMTVNSLQCHQHKAWRFGGRFMNFIKEAQWEGLT  344 humEAA5b   295  LYDAVHIVSVCYQRAPQMTVNSLQCHRHKAWRFGGRFMNFIKEAQWEGLT  344 humEAA5a   804  SVLVAVGEFVYKLRKTAEREQRSFCSTVADEIRFSLTCQRRVKHKPQPPM  889 humEAA5c   804  SVLVAVGEFVYKLRKTAEREQRSFCSTVADEIRFSPP*              840
```

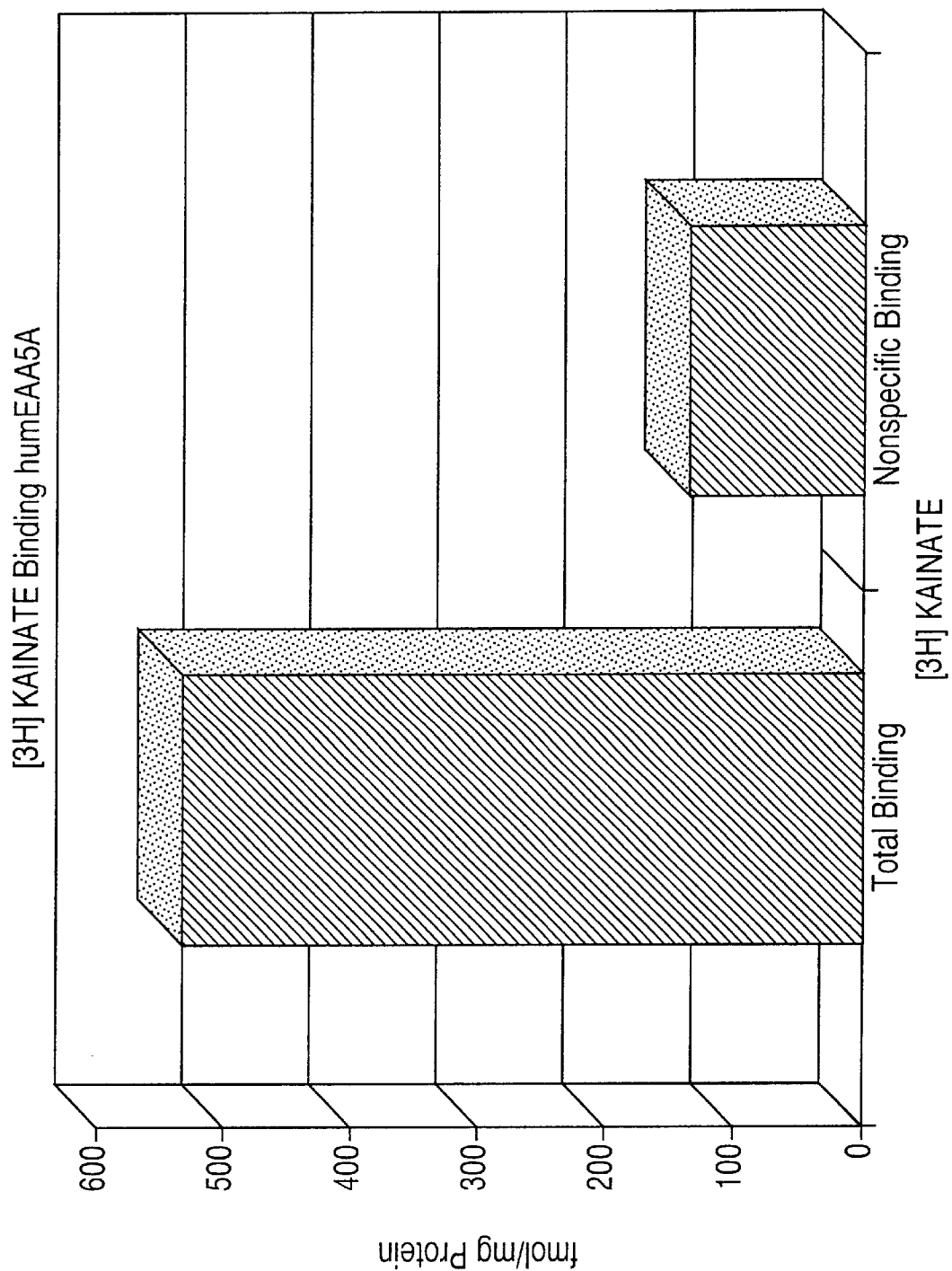

KAINATE-BINDING, HUMAN CNS RECEPTORS OF THE EAA5 FAMILY

This application is a division, of application Ser. No. 07/945,210, filed Sep. 17, 1992, now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impluses is controlled by the interaction between a neurotransmitter substance released by the "sending" neuron which then binds to a surface receptor on the "receiving" neuron, to cause excitation thereof. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (α-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The glutamate-binding EAA receptor family is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided, for drug screening programs.

Non-human genes which appear to encode the kainate-type of receptor have also been reported. Egebjerg et al., Nature 351: 745, 1991, have described the isolation of a gene from rat called GluR6, which although related by sequence to the AMPA receptor genes, forms a receptor which is not activated by AMPA but rather by glutamate, quisqualate, and preferentially, kainate (see also WO91/06648). Similar activity has been ascribed to the product of another rat gene, GluR7, as reported by Bettler et al, Neuron, 1992, 8:257. Still other kainate-binding proteins have been described from frog (Wada et al., Nature 342: 684, 1989), chicken (Gregor et al., Nature 342: 689, 1989) and from rat (Werner et al., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA5a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA5a receptor have also been identified, and constitute additional members of this receptor family, herein referred to as the human EAA5 receptor family.

The present invention thus provides, in one of its aspects, an isolated polynucleotide, consisting either of DNA or of RNA, which codes for a human EAA5 receptor or for a kainate-binding fragment thereof.

In another aspect of the present invention, there is provided a cell that has been genetically engineered to produce a kainate-binding, human EAA receptor belonging to the herein-defined EAA5 family. In related aspects of the present invention, there are provided recombinant DNA constructs and relevant methods useful to create such cells.

In another aspect of the present invention, there is provided a method for evaluating interaction between a test ligand and a human EAA receptor, which comprises the steps of incubating the test ligand with a genetically engineered cell of the present invention, or with a membrane preparation derived therefrom, and then assessing said interaction by determining receptor/ligand binding.

Other aspects of the present invention, which encompass various applications of the discoveries herein described, will become apparent from the following detailed description, and from the accompanying drawings, in which:

BRIEF REFERENCE TO THE DRAWINGS

FIGS. 1A–1L (SEQ ID NOS. 1 and 2) provides the nucleotide sequence of a cDNA insert comprising DNA coding for an excitatory amino acid receptor of the present invention, and the deduced amino acid sequence thereof;

FIGS. 3A and 3B (SEQ ID NOS. 3–10) show, with reference to FIGS. 1A–1L, the DNA and amino acid sequences of naturally occurring variants of the EAA receptor illustrated in FIGS. 1A–1L; and FIG. 4 illustrates the ligand-binding property of an EAA receptor expressed from the coding region provided in FIGS. 1A–1L.

DETAILED DESCRIPTION OF THE INVENTION AND ITS PREFERRED EMBODIMENTS

Figure 2:
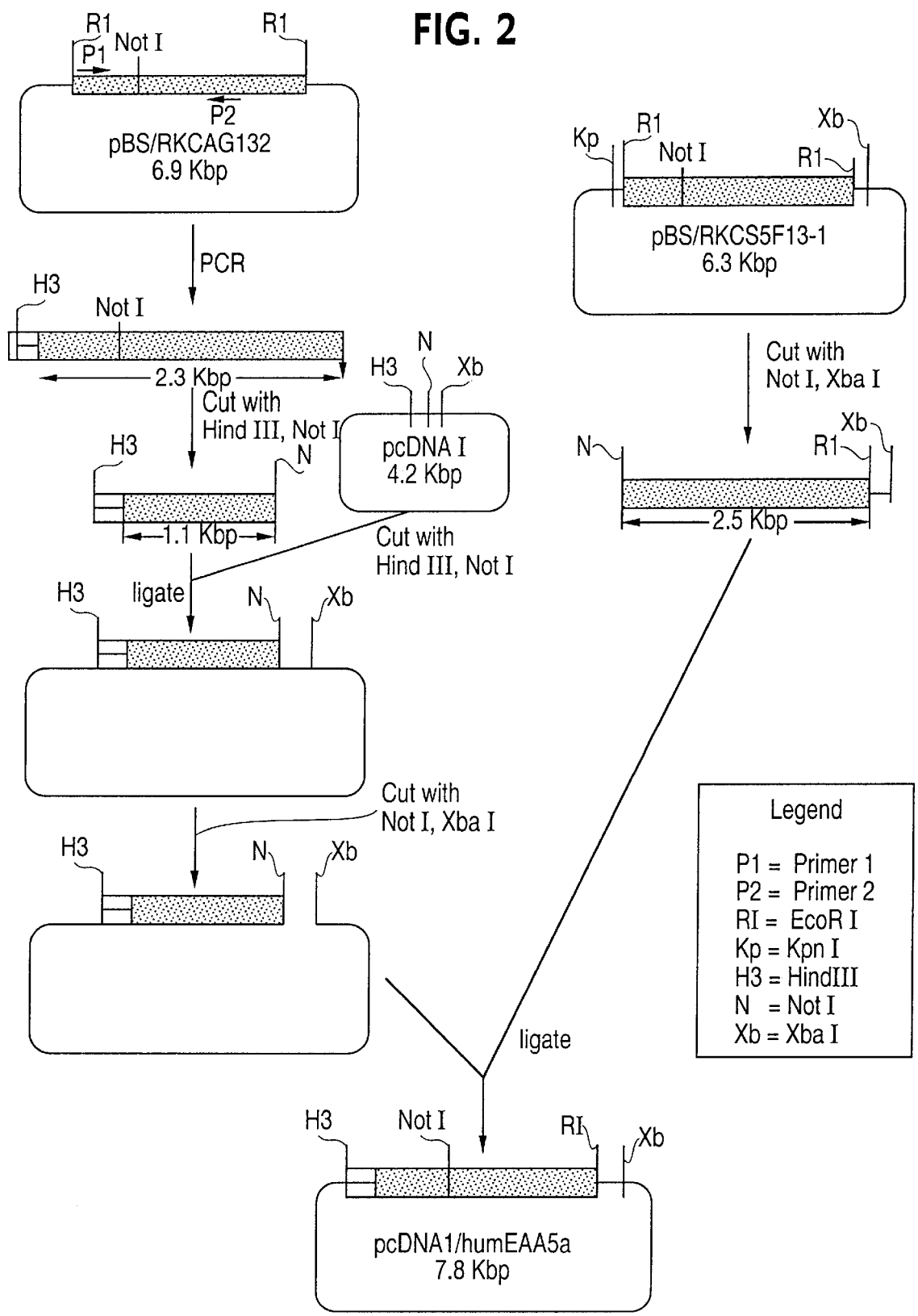
FIG. 2 illustrates with linear plasmid maps the strategy used to construct expression vectors harbouring the DNA sequence illustrated in FIGS. 1A–1L.

The invention relates to excitatory amino acid (EAA) receptors of human origin, and is directed more particularly to a novel family of kainate-type human EAA receptors, herein designated the human EAA5 receptor family. As used herein, the term "human EAA5 receptor" is intended to embrace the human EAA5a receptor, and kainate-binding variants of the EAA5a receptor that are structurally related thereto, i.e. share at least 99% amino acid identity, including naturally occurring and synthetically derived variants of the EAA5a receptor. Naturally occurring variants of the human EAA5a receptor include particularly the receptors herein designated human EAA5b receptor and human EAA5c receptor. Synthetically derived variants of the human EAA5a receptor include kainate-binding variants that incorporate one or more, e.g. 1–10, amino acid substitutions, deletions or additions, relative to the EAA5a receptor.

As used herein, the term "kainate-binding" refers to receptor variants and receptor fragments that display greater binding affinity for kainate than for either glutamate, AMPA or NMDA, as determined in assays of conventional design, such as the assays herein described.

Each of the naturally occurring members of the EAA5 receptor family possesses structural features characteristic of the EAA receptors in general, including extracellular N- and C-terminal regions, as well as four internal hydrophobic domains which serve to anchor the receptor within the cell surface membrane. The particular human EAA receptor designated EAA5a is a protein characterized structurally as a single polypeptide chain that is produced initially in a precursor form bearing a 31 residue N-terminal signal peptide, and is transported to the cell surface in mature form, lacking the signal peptide and consisting of 888 amino acids arranged in the sequence illustrated, by single letter code, in FIGS. 1A–1L (SEQ ID NOS. 1 and 2). Unless otherwise stated, the term "EAA5 receptor" refers to the mature form of the receptor protein, and amino acid residues of the EAA5 receptors are accordingly numbered with reference to the mature protein sequence. With respect to structural domains of the receptor, hydropathy analysis of the EAA5a receptor reveals four putative transmembrane domains, one spanning residues 534–553 inclusive (TM-1), another spanning residues 574–595 (TM-2), a third spanning residues 606–624 (TM-3) and the fourth spanning residues 791–811 (TM-4), all of SEQ ID NOS. 1 and 2) Based on this assignment, it is likely that the human EAA5a receptor structure, in its natural membrane-bound form, consists of a 533 amino acid N-terminal extracellular domain, followed by a hydrophobic region containing four transmembrane domains and an extracellular, 77 amino acid C-terminal domain.

As shown in FIGS. 3A and 3B, two structurally related variants of the EAA5a receptor, which occur naturally in human brain tissue, have also been identified, and are designated the EAA5b partial sequences of which are shown in (SEQ ID NOS. 4 and 8) receptor and the EAA5c partial sequences of which are shown in (SEQ ID NOS. 6 and 10) receptor. As deduced from nucleotide sequences of the genes coding for them, the EAA5b variant shares greater than 99% amino acid identity with EAA5a partial sequences of which are shown in (SEQ ID NOS. 3, 5, 7 and 9), differing with respect only to a single amino acid change at position 321, which in the EAA5a receptor is a glutamine residue and in the EAA5b receptor is an arginine residue. The EAA5c receptor, on the other hand, is a C-terminally truncated version of EAA5a, which in addition to the 48 amino acid C-terminal truncation incorporates amino acid replacements in the last two positions. Region of the DNA and amino acid sequences of the EAA5b and EAA5c receptors are illustrated in FIGS. 3A and 3B by comparison to regins of the EAA5a DNA and amino acid sequences.

Like other members of the human EAA5 receptor family, receptor subtype EAA5a is characterized by a pharmacological profile i.e. a ligand binding "signature", that points strongly to a kainate-type pharmacology, as distinct from other excitatory amino acid receptor types, such as NMDA and AMPA. In addition and despite the understanding that kainate binding receptors require a multi- and perhaps heteromeric subunit structure to function in the pharmacological sense, it has been found that cells producing the unitary EAA5a receptor do, independently of association with other receptor subunits, provide a reliable indication of excitatory amino acid binding. Thus, in a key aspect of the present invention, the human EAA5a receptor is exploited for the purpose of screening candidate compounds for the ability to interact with the present receptors and/or the ability to compete with endogenous EAA receptor ligands and known synthetic analogues thereof, for EAA receptor interaction.

For use in assessing interaction between the receptor and a test ligand, it is desirable to construct by application of genetic engineering techniques a mammalian cell that produces a human EAA5 receptor in functional form as a heterologous product. The construction of such cell lines is achieved by introducing into a selected host cell a recombinant DNA construct in which DNA coding for a secretable form of the human EAA5 receptor,i.e., a form bearing either its native signal peptide or a functional, heterologous equivalent thereof, is associated with expression controlling elements that are functional in the selected host to drive expression of the receptor-encoding DNA, and thus elaborate the desired EAA5 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host.

The particular cell type selected to serve as host for production of the human EAA5 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for EAA5 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C 127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA5 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for a secretable form of the receptor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E.coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals i.e. the metallothionein gene promoter, and other steroid-inducible promoters.

For incorporation into the recombinant DNA expression vector, DNA coding for the desired EAA5 receptor, e.g. the EAA5a receptor or a kainate-binding variant thereof, can be obtained by applying selected techniques of gene isolation or gene synthesis. As described in more detail in the examples herein, the EAA5a receptor, and the EAA5b variant thereof, are encoded within the genome of human brain tissue, and can therefore be obtained by careful application of conventional gene isolation and cloning techniques. This typically will entail extraction of total messenger RNA from a fresh source of human brain tissue, such as cerebellum or hippocampus tissue and preferably fetal brain tissue, followed by conversion of message to cDNA and formation of a library in for example a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA5 receptors, it will be appreciated that automated techniques of gene synthesis and/or amplification can be performed to generate DNA coding therefor. Because of the length of EAA5 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA5 gene family. It will be appreciated, for example and as mentioned above, that polynucleotides coding for the EAA5 receptors herein described can be generated by substituting synonymous codons for those represented in the naturally occurring polynucleotide sequences herein identified. In addition, polynucleotides coding for synthetic variants of the EAA5 receptors herein described can be generated which for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, microinjection, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the E. coli gpt gene which confers resistance to mycophenolic acid, the neo gene from transposon Tn5 which confers resistance to the antibiotic G418 and to neomycin, the dhfr sequence from murine cells or E. coli which changes the phenotype of DHFR– cells into DHFR+ cells, and the tk gene of herpes simplex virus, which makes TK–cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

As an alternative to using cells that express receptor-encoding DNA, ligand characterization may also be performed using cells, for example Xenopus oocytes, that yield functional membrane-bound receptor following introduction of messenger RNA coding for the EAA5 receptor. In this case, the EAA5 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested in either intact or membrane preparations form for the ability to bind a particular ligand molecule supplied in a bathing solution.

The binding of a candidate ligand to a selected human EAA5 receptor of the invention is evaluated typically using a predetermined amount of cell-derived membrane (measured for example by protein determination), generally from about 25 ug to 100 ug. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that kainate-binding fragments, i.e., the portion of the EAA5 receptor responsible for binding a ligand molecule, resides on the outside of the cell, i.e., is extracellular. It is therefore desirable in the first instance to facilitate the characterization of the receptor-ligand interaction by providing such kainate binding fragments in quantity and in isolated form, i.e., free from the remainder of the receptor. To accomplish this, the full-length EAA5 receptor-encoding DNA may be modified by site-directed mutagenesis, so as to introduce a translational stop codon into the extracellular N-terminal region, immediately before the sequence encoding the first transmembrane domain (TM1), i.e., before residue 534 as shown in FIGS. 1A–1L (SEQ ID NOS. 1 and 2). Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 812 and 888 inclusive of FIGS. 1A–1L (SEQ ID NOS. 1 and 2). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. *Aspergillus nidulans*, for example, with the expression being driven by the alcA promoter, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

For use particularly in detecting the presence and/or location of an EAA5 receptor, for example in brain tissue, the present invention also provides, in another of its aspects, labelled antibody to a human EAA5 receptor. To raise such antibodies, there may be used as immunogen either the intact, soluble receptor or an immunogenic fragment thereof, produced in a microbial or mammalian cell host as described above or by standard peptide synthesis techniques. Regions of the EAA5a receptor particularly suitable for use as immunogenic fragments include those corresponding in sequence to an extracellular region of the receptor, or a portion of the extracellular region, such as peptides consisting of residues 1–533, including particularly residues 187–202 or 486–529, and peptides corresponding to the region between transmembrane domains TM-2 and TM-3, such as a peptide consisting of residues 596–605 (SEQ ID NO: 1). Peptides consisting of the C-terminal domain (residues 812–888), or fragment thereof may also be used for the raising of antibodies. Substantially the same region of the human EAA5b receptor may also be used for production of antibodies against this receptor.

The raising of antibodies to the desired EAA5 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA5 receptor, and selected regions thereof, may also be used, in accordance with another aspect of the present invention, as hybridization probes for example to identify sequence-related genes resident in the human or other mammalian genomes (or cDNA libraries) or to locate the EAA5-encoding DNA in a specimen, such as brain tissue. This can be done using either the intact coding region, or a fragment thereof having radiolabelled e.g. $^{32}P$, nucleotides incorporated therein. To identify the EAA5-encoding DNA in a specimen, it is desirable to use either the full length cDNA coding therefor, or a fragment which is unique thereto. With reference to FIGS. 1A–1L (SEQ ID NOS: 1 and 2) and the nucleotide numbering appearing thereon, such nucleotide fragments include those comprising at least about 17 nucleic acids, and otherwise corresponding in sequence to a region coding for the N-terminus or C-terminus of the receptor, or representing a 5'-untranslated or 3'-untranslated region thereof. These sequences, and the intact gene itself, may also be used of course to clone EAA5-related human genes, particularly cDNA equivalents thereof, by standard hybridization techniques.

EXAMPLE 1

Isolation of DNA Coding for the Human EAA5a Receptor cDNA coding for the human EAA5a receptor was identified by probing human fetal brain cDNA that was obtained as an EcoRi-based lambda phage library (lambda ZAP) from Stratagene Cloning Systems (La Jolla, Calif., U.S.A.). The cDNA library was screened using an oligonucleotide probe capable of annealing to the 3' region of the rat GluR5 receptor sequence reported by Bettler et al in Neuron, 1990, 5:583. The specific sequence (SEQ ID NO: 11) of the $^{32}P$-labelled probe is provided below:

5'-ATCGGCGGCATCTTCATTGTTCTGGCTGCAG GACTCGTGC-3'

The fetal brain cDNA library was screened under the following hybridization conditions; 6×SSC, 25% formamide, 5×Denhardt's solution, 10 mM Na2HPO4 buffer, 0.5% sodium pyrophosphate, 0.5% SDS, 100 µg/ml denatured salmon sperm DNA, 42° C. Filters were washed with 6×SSC containing 0.5% SDS at 25° C. for 5 minutes, followed by a 15 minute wash at 42° C. with 2×SSC containing 0.5% SDS. The final wash was with 1×SSC containing 0.5% SDS at 50° C. for 15 minutes. Filters were exposed to X-ray film (Kodak) overnight. Of $10^6$ clones screened, only two cDNA inserts were identified; one about 3.3 kb designated RKCS5F131, and another about 2.7 kb designated RKCS5F81. For sequencing, the '131 and '81 phages were plaque purified, then excised as phagemids according to the supplier's specifications, to generate insert-carrying Bluescript-SK variants of the phagemid vectors. Sequencing of the '131 clone across its entire sequence revealed a termination codon together with about 859 bases of 3'non-coding region and about 2.4 kb of coding region. Sequencing across the '81 insert revealed a significant overlap with '131, and provided some additional 5'sequence, although no putative ATG initiation codon was located.

There being no initiation codon apparent in the '81 sequence, a 5' region of the gene was sought. For this purpose, a 0.65 kb EcoRI fragment representing the 5'end of '81 was isolated, $^{32}P$-labelled, and then used to re-screen the same fetal brain cDNA library under the following hybridization conditions: 6×SSC, 25% formamide, 5×Denhardt's solution, 0.5% SDS, 100 µg/ml denatured salmon sperm DNA, 42° C. Filters were washed twice with 2×SSC containing 0.5% SDS at 25° C. for 5 minutes, followed by a 15 minute final wash at 42° C. with 2×SSC containing 0.5%

SDS. This identified two inserts, one about 3.9 kb designated RKCAG132, and another about 3.3 kb designated RKCAG112. Sequencing the entire '132 insert revealed some additional 5'sequence but still did not reveal an initiation codon. The '112 insert, when sequenced, revealed the initiation codon together with about 24 bases of 5'non-coding region and a significant overlap with the '132 insert.

As a first step to providing the entire coding region in an intact clone, there were synthesized two oligonucleotide primers capable of hybridizing with the sequence-related regions in the '132 insert. The 5'primer was designed to incorporate the non-hybridizing flank bearing a consensus Kozak sequence (a consensus translation initiation sequence as reported by Kozak, Nucl. Acids Res., 1987, 15:8125), a putative ATG initiation codon and 5'sequence of the '112 insert, as well as a HindIII restriction site to facilitate subsequent cloning work. The sequences of the two primers (SEQ ID NOS. 12 and 13, respectively), synthesized using conventional techniques, are presented below:
primer 1:
5'-GGGGTTAAGCTTGCCGCCACCATGACCGCTCC CTGGCGGCGCCTCCGGAGTCT-3'
primer 2: 5'-CAGGGCACTGGCCTCTTTGT-3'
Using '132 DNA as template, the primers were then used to amplify by polymerase chain reaction (PCR) the sequence containing the consensus Kozak sequence, initiation codon and 5'sequence common to the '112 insert. Reaction mixtures contained, in 100 µl, 10 ng of '132 DNA, 125 pmol of each primer and 2U Taq polymerase (in 10 mM Tris-HCl, pH9.0, 50 mM KCl, 1.5 mM $MgCl_2$, and with 0.2 mM of each deoxyribonucleotide species). There were then performed 4 cycles of 95° C./1 min; 60° C./30 sec; 72° C./2 min, followed by 21 cycles of 95° C./1 min; 72° C./2 min 30 sec, followed by a final cycle of 72° C./10 min. An amplified product having the expected 2.7 kb length was generated.

To provide the entire coding region of the receptor, the strategy depicted in FIG. 2 was then applied to generate the phagemid pcDNAI/humEAA5a which carries the intact EAA5a receptor-encoding DNA as a 3.6 kb HindIII/EcoRI insert in a 4.2 kb pcDNAI phagemid background. The 4.2 kb phagemid pcDNA1 is available commercially from Invitrogen Corporation (San Diego, Calif., USA; catalogue number V490-20). This is a multifunctional vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter). The entire sequence of the receptor-encoding HindIII/EcoRI insert incorporated on the pcDNAI vector is provided in FIG. 1 (SEQ ID NOS. 1 and 2).

The 7.8 kb phagemid designated pcDNAI/humEAA5a, carrying the receptor-encoding DNA as a 3.6 kb HindIII/EcoRI insert in a 4.2 kb pcDNAI phagemid background was deposited under the terms of the Budapest Treaty with the American Type Culture Collection in Rockville, Md. USA on Aug. 26, 1992, and has been assigned accession number ATCC 75296.

EXAMPLE 2

Construction of Genetically Engineered Cells Producing the Human EAA5a Receptor

For expression in a mammalian cell host, pcDNAI/humEAA5a, obtained as described in example 1, was introduced for transient expression into monkey-derived, fibroblast like cells of the COS-1 lineage (available from the American Type Culture Collection, Rockville, Md. as ATCC CRL 1650).

For transient expression of the EAA5a-encoding DNA, COS-1 cells were transfected with approximately 8 ug DNA (as pcDNAI/humEAA5a) per $10^6$ COS cells, by DEAE-mediated DNA transfection and treated with chloroquine according to the conventional procedures. Briefly, COS-1 cells were plated at a density of $5 \times 10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 µM chloroquine, 10% NuSerum, DNA (0.4 mg/ml) in DMEM/F12 medium. After incubation for 3 hours at 37° C., cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines can also be prepared using two different cell types as host: CHO K1 and CHO Pro5. To construct these cell lines, cDNA coding for human EAA5a is incorporated into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells are first seeded at a density of $5 \times 10^5$ in 10% FBS-supplemented αMEM medium. After growth for 24 hours, fresh medium is added to the plates and three hours later, the cells are transfected using the calcium phosphate-DNA co-precipitation procedure (Maniatis et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2–3 weeks later, clonally selected and then propogated for assay purposes.

EXAMPLE 3

Ligand Binding Assays

Transfected cells in the frozen state were resuspended in ice-cold distilled water using a hand homogenizer and centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and centrifuged again at 50,000 g for 10 minutes in order to remove endogenous glutamate that would compete for binding. Pellets were resuspended in ice cold 50 mM Tris-HCl (pH 7.55) buffer and the resultant membrane preparation was used as tissue source for binding experiments described below. Proteins were determined using the Pierce Reagent with BSA as standard.

Binding assays were then performed, using an amount of COS-derived membrane equivalent to 25–100 ug as judged by protein determination and selected radiolabelled ligand. In particular, for kainate binding assays, incubation mixtures consisted of 25–100 μg tissue protein and [vinylidene-3H] kainic acid (58 Ci/mmole, 85 nM final) in the cold incubation buffer, 1 ml final volume. Non-specific binding was in the presence of 1 mM L-glutamate. Samples were incubated on ice for 60 minutes, and bound and free ligand were then separated by rapid filtration using a PHD cell harvester and GF/B filters pre-soaked in ice-cold 0.3% polyethyleneimine. Filters were washed twice in 4 ml of the cold incubation buffer, then placed in scintillation vials with 5 ml of Beckman Ready-Protein Plus scintillation cocktail for counting.

For AMPA-binding assays, incubation mixtures consisted of 25–100 ug tissue protein and D,L-α-[5-methyl-3H] amino-3-hydroxy-5-methylisoxazole-4-propionic acid (3H-AMPA, 27.6 Ci/mmole, 10 nM final) with 0.1M KSCN and 2.5 mM $CaCl_2$ in the 1 ml final volume. Non-specific binding was determined in the presence of 1 mM L-glutamate. Samples were incubated on ice for 60 minutes in plastic minivials, and bound and free ligand were separated by centrifugation for 30 minutes at 50,000 g. Pellets were washed twice in 4 ml of the cold incubation buffer, then 5 ml of Beckman Ready-Protein Plus scintillation cocktail was added, for counting.

Assays performed in this manner, using membrane preparations derived from the EAA5a-producing COS cells, revealed specific [3H]-kainate binding at 40 nM, labelled ligand (FIG. 4). Mock transfected cells exhibited no specific binding of any of the ligands tested. These results demonstrate clearly that the human EAA5a receptor is binding kainate specifically. This activity, coupled with the fact that there is little or no demonstrable binding of either AMPA or NMDA clearly assigns the EAA5a receptor to be of the kainate type of EAA receptor. Furthermore, this binding profile indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA5a receptor gene in a pure form, capable of being expressed as a single, homogenous receptor species, therefore frees the ligand binding assay from the lack of precision introduced when complex, heterogeneous receptor preparations from human brains are used to attempt such characterizations.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 3619 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: sig_peptide
      (B) LOCATION: 16..108

(ix) FEATURE:
      (A) NAME/KEY: mat_peptide
      (B) LOCATION: 109..2772

(ix) FEATURE:
      (A) NAME/KEY: CDS
      (B) LOCATION: 16..2772

(xi) SEQUENCE DESCRIPTION: SEQ ID NO:1:

```
AAGCTTGCCG CCACC ATG ACC GCT CCC TGG CGG CGC CTC CGG AGT CTG GTT         51
              Met Thr Ala Pro Trp Arg Arg Leu Arg Ser Leu Val
              -31 -30              -25                 -20

TGG GAA TAC TGG GCC GGG CTC CTC GTG TGC GCC TTC TGG ATC CCG GAC          99
Trp Glu Tyr Trp Ala Gly Leu Leu Val Cys Ala Phe Trp Ile Pro Asp
            -15              -10                  -5

TCG CGC GGG ATG CCC CAC GTC ATC CGG ATC GGA GGA ATC TTC GAG TAT        147
```

-continued

```
Ser Arg Gly Met Pro His Val Ile Arg Ile Gly Gly Ile Phe Glu Tyr
          1               5                  10

GCG GAC GGC CCC AAC GCC CAG GTC ATG AAT GCC GAG GAG CAT GCC TTT      195
Ala Asp Gly Pro Asn Ala Gln Val Met Asn Ala Glu Glu His Ala Phe
 15                  20                  25

CGA TTT TCT GCC AAC ATC ATC AAC AGG AAC AGG ACT CTG CTG CCC AAC      243
Arg Phe Ser Ala Asn Ile Ile Asn Arg Asn Arg Thr Leu Leu Pro Asn
 30                  35                  40                  45

ACA ACC TTG ACC TAT GAC ATA CAG AGG ATT CAC TTC CAT GAC AGC TTC      291
Thr Thr Leu Thr Tyr Asp Ile Gln Arg Ile His Phe His Asp Ser Phe
                 50                  55                  60

GAG GCG ACC AAA AAG GCC TGT GAC CAG CTG GCA CTG GGC GTG GTG GCG      339
Glu Ala Thr Lys Lys Ala Cys Asp Gln Leu Ala Leu Gly Val Val Ala
             65                  70                  75

ATC TTC GGC CCA TCA CAG GGC TCC TGC ACC AAT GCC GTC CAG TCC ATC      387
Ile Phe Gly Pro Ser Gln Gly Ser Cys Thr Asn Ala Val Gln Ser Ile
         80                  85                  90

TGC AAT GCC CTG GAG GTG CCC CAC ATC CAG CTG CGT TGG AAG CAC CAC      435
Cys Asn Ala Leu Glu Val Pro His Ile Gln Leu Arg Trp Lys His His
     95                 100                 105

CCG CTG GAC AAC AAG GAC ACC TTC TAC GTG AAC CTC TAC CCC GAC TAC      483
Pro Leu Asp Asn Lys Asp Thr Phe Tyr Val Asn Leu Tyr Pro Asp Tyr
110                 115                 120                 125

GCC TCG CTC AGC CAT GCC ATC CTC GAC CTG GTC CAG TAC CTC AAG TGG      531
Ala Ser Leu Ser His Ala Ile Leu Asp Leu Val Gln Tyr Leu Lys Trp
                130                 135                 140

CGG TCG GCC ACC GTG GTC TAT GAC GAC AGT ACA GGG CTC ATC CGA CTG      579
Arg Ser Ala Thr Val Val Tyr Asp Asp Ser Thr Gly Leu Ile Arg Leu
            145                 150                 155

CAG GAG CTC ATC ATG GCC CCA TCA AGA TAC AAC ATC CGC CTG AAG ATC      627
Gln Glu Leu Ile Met Ala Pro Ser Arg Tyr Asn Ile Arg Leu Lys Ile
        160                 165                 170

CGT CAG CTC CCC ATC GAC TCT GAC GAC TCG CGC CCC TTG CTC AAG GAG      675
Arg Gln Leu Pro Ile Asp Ser Asp Asp Ser Arg Pro Leu Leu Lys Glu
175                 180                 185

ATG AAG CGA GGC CGG GAA TTC CGC ATT ATC TTC GAC TGC AGC CAC ACT      723
Met Lys Arg Gly Arg Glu Phe Arg Ile Ile Phe Asp Cys Ser His Thr
190                 195                 200                 205

ATG GCG GCC CAG ATC CTC AAG CAG GCC ATG GCC ATG GGC ATG ATG ACT      771
Met Ala Ala Gln Ile Leu Lys Gln Ala Met Ala Met Gly Met Met Thr
                210                 215                 220

GAG TAC TAC CAC TTC ATC TTC ACC ACT CTG GAT CTC TAC GCT TTA GAC      819
Glu Tyr Tyr His Phe Ile Phe Thr Thr Leu Asp Leu Tyr Ala Leu Asp
            225                 230                 235

CTG GAG CCC TAC CGC TAC TCA GGC GTG AAC CTG ACA GGA TTC CGG ATT      867
Leu Glu Pro Tyr Arg Tyr Ser Gly Val Asn Leu Thr Gly Phe Arg Ile
        240                 245                 250

CTC AAT GTG GAC AAC CCA CAC GTC TCG GCC ATT GTG GAG AAG TGG TCC      915
Leu Asn Val Asp Asn Pro His Val Ser Ala Ile Val Glu Lys Trp Ser
255                 260                 265

ATG GAG CGG CTG CAG GCA GCT CCC CGG GCC GAG TCT GGC CTG CTG GAT      963
Met Glu Arg Leu Gln Ala Ala Pro Arg Ala Glu Ser Gly Leu Leu Asp
270                 275                 280                 285

GGA GTA ATG ATG ACT GAT GCA GCC TTA CTG TAC GAC GCC GTC CAT ATC     1011
Gly Val Met Met Thr Asp Ala Ala Leu Leu Tyr Asp Ala Val His Ile
                290                 295                 300

GTG TCC GTG TGC TAC CAG CGG GCA CCA CAG ATG ACC GTG AAC TCC CTG     1059
Val Ser Val Cys Tyr Gln Arg Ala Pro Gln Met Thr Val Asn Ser Leu
            305                 310                 315
```

-continued

```
CAG TGC CAT CAG CAC AAG GCC TGG CGC TTT GGC GGC CGC TTC ATG AAC    1107
Gln Cys His Gln His Lys Ala Trp Arg Phe Gly Gly Arg Phe Met Asn
320                 325                 330

TTC ATC AAG GAG GCT CAA TGG GAA GGA TTA ACT GGA CGA ATT GTT TTC    1155
Phe Ile Lys Glu Ala Gln Trp Glu Gly Leu Thr Gly Arg Ile Val Phe
    335                 340                 345

AAC AAA ACT AGT GGC TTG CGG ACG GAT TTT GAT CTG GAC ATC ATC AGC    1203
Asn Lys Thr Ser Gly Leu Arg Thr Asp Phe Asp Leu Asp Ile Ile Ser
350                 355                 360                 365

CTG AAA GAG GAT GGC CTG GAG AAG GTT GGG GTG TGG AGT CCT GCC GAC    1251
Leu Lys Glu Asp Gly Leu Glu Lys Val Gly Val Trp Ser Pro Ala Asp
            370                 375                 380

GGG CTC AAC ATC ACT GAG GTT GCC AAA GGC CGA GGC CCT AAT GTC ACC    1299
Gly Leu Asn Ile Thr Glu Val Ala Lys Gly Arg Gly Pro Asn Val Thr
                385                 390                 395

GAC TCT CTG ACA AAC AGA TCA CTC ATT GTC ACC ACA GTG CTG GAG GAG    1347
Asp Ser Leu Thr Asn Arg Ser Leu Ile Val Thr Thr Val Leu Glu Glu
    400                 405                 410

CCC TTC GTC ATG TTT CGG AAA TCA GAC AGG ACG CTA TAT GGG AAT GAC    1395
Pro Phe Val Met Phe Arg Lys Ser Asp Arg Thr Leu Tyr Gly Asn Asp
415                 420                 425

CGG TTC GAG GGC TAC TGC ATC GAC CTG CTA AAG GAG CTG GCC CAC ATC    1443
Arg Phe Glu Gly Tyr Cys Ile Asp Leu Leu Lys Glu Leu Ala His Ile
430                 435                 440                 445

CTT GGT TTC TCC TAT GAG ATC CGG CTG GTG GAG GAC GGC AAG TAC GGG    1491
Leu Gly Phe Ser Tyr Glu Ile Arg Leu Val Glu Asp Gly Lys Tyr Gly
            450                 455                 460

GCA CAG GAT GAC AAG GGC CAG TGG AAC GGC ATG GTC AAG GAG CTC ATC    1539
Ala Gln Asp Asp Lys Gly Gln Trp Asn Gly Met Val Lys Glu Leu Ile
                465                 470                 475

GAC CAC AAG GCA GAT CTG GCC GTG GCC CCC CTG ACC ATC ACC CAT GTT    1587
Asp His Lys Ala Asp Leu Ala Val Ala Pro Leu Thr Ile Thr His Val
    480                 485                 490

CGA GAG AAG GCC ATC GAC TTC TCC AAG CCC TTC ATG ACA CTT GGT GTG    1635
Arg Glu Lys Ala Ile Asp Phe Ser Lys Pro Phe Met Thr Leu Gly Val
495                 500                 505

AGC ATC CTG TAT CGA AAG CCC AAT GGC ACC AAC CCC AGC GTC TTC TCC    1683
Ser Ile Leu Tyr Arg Lys Pro Asn Gly Thr Asn Pro Ser Val Phe Ser
510                 515                 520                 525

TTC CTC AAT CCC CTG TCC CCA GAC ATC TGG ATG TAT GTT CTC CTC GCC    1731
Phe Leu Asn Pro Leu Ser Pro Asp Ile Trp Met Tyr Val Leu Leu Ala
            530                 535                 540

TAC CTG GGG GTC AGC TGT GTC CTC TTC GTC ATC GCC AGG TTC AGC CCT    1779
Tyr Leu Gly Val Ser Cys Val Leu Phe Val Ile Ala Arg Phe Ser Pro
                545                 550                 555

TAT GAG TGG TAC GAT GCT CAC CCC TGC AAC CCT GGC TCC GAG GTG GTG    1827
Tyr Glu Trp Tyr Asp Ala His Pro Cys Asn Pro Gly Ser Glu Val Val
    560                 565                 570

GAA AAT AAC TTC ACT CTG CTT AAC AGC TTC TGG TTT GGA ATG GGA TCC    1875
Glu Asn Asn Phe Thr Leu Leu Asn Ser Phe Trp Phe Gly Met Gly Ser
575                 580                 585

CTG ATG CAG CAA GGG TCT GTG CTG ATG CCC AAA GCC CTG TCC ACA CGC    1923
Leu Met Gln Gln Gly Ser Val Leu Met Pro Lys Ala Leu Ser Thr Arg
590                 595                 600                 605

ATC ATT GGT GGC ATC TGG TGG TTC TTT ACG CTC ATC ATC ATC TCT TCC    1971
Ile Ile Gly Gly Ile Trp Trp Phe Phe Thr Leu Ile Ile Ile Ser Ser
            610                 615                 620

TAC ACG GCC AAC CTG GCT GCC TTT CTG ACC GTG GAG CGC ATG GAA TCA    2019
Tyr Thr Ala Asn Leu Ala Ala Phe Leu Thr Val Glu Arg Met Glu Ser
                625                 630                 635
```

```
CCC ATT GAC TCT GCT GAT GAC CTG GCC AAG CAA ACC AAA ATC GAG TAT   2067
Pro Ile Asp Ser Ala Asp Asp Leu Ala Lys Gln Thr Lys Ile Glu Tyr
            640                 645                 650

GGG GCT GTC AAG GAT GGG GCC ACC ATG ACC TTC TTC AAG AAA TCC AAG   2115
Gly Ala Val Lys Asp Gly Ala Thr Met Thr Phe Phe Lys Lys Ser Lys
            655                 660                 665

ATC TCC ACC TTC GAG AAG ATG TGG GCC TTC ATG AGC AGG AAG CCA TCG   2163
Ile Ser Thr Phe Glu Lys Met Trp Ala Phe Met Ser Arg Lys Pro Ser
670                 675                 680                 685

GCG CTG GTG AAG AAC AAC GAG GAG GGC ATC CAG AGG GCC CTG ACG GCC   2211
Ala Leu Val Lys Asn Asn Glu Glu Gly Ile Gln Arg Ala Leu Thr Ala
                690                 695                 700

GAC TAC GCG CTG CTC ATG GAG TCC ACC ACC ATC GAG TAC GTC ACG CAG   2259
Asp Tyr Ala Leu Leu Met Glu Ser Thr Thr Ile Glu Tyr Val Thr Gln
        705                 710                 715

AGG AAC TGC AAC CTC ACC CAG ATC GGG GGC CTC ATT GAC TCC AAG GGC   2307
Arg Asn Cys Asn Leu Thr Gln Ile Gly Gly Leu Ile Asp Ser Lys Gly
        720                 725                 730

TAC GGC ATC GGC ACG CCC ATG GGC TCC CCA TAC CGG GAC AAG ATC ACC   2355
Tyr Gly Ile Gly Thr Pro Met Gly Ser Pro Tyr Arg Asp Lys Ile Thr
735                 740                 745

ATC GCC ATC CTG CAG CTT CAG GAG GAG GAC AAG CTG CAT ATC ATG AAG   2403
Ile Ala Ile Leu Gln Leu Gln Glu Glu Asp Lys Leu His Ile Met Lys
750                 755                 760                 765

GAG AAG TGG TGG CGG GGC AGC GGG TGT CCT GAG GAG GAA AAC AAA GAG   2451
Glu Lys Trp Trp Arg Gly Ser Gly Cys Pro Glu Glu Glu Asn Lys Glu
                770                 775                 780

GCC AGT GCC CTG GGG ATC CAG AAG ATC GGG GGC ATC TTC ATT GTC CTG   2499
Ala Ser Ala Leu Gly Ile Gln Lys Ile Gly Gly Ile Phe Ile Val Leu
            785                 790                 795

GCC GCC GGG CTG GTC CTC TCT GTG CTG GTG GCC GTG GGC GAG TTT GTG   2547
Ala Ala Gly Leu Val Leu Ser Val Leu Val Ala Val Gly Glu Phe Val
            800                 805                 810

TAC AAG CTC CGC AAA ACA GCA GAG AGA GAG CAG CGT TCC TTC TGC AGC   2595
Tyr Lys Leu Arg Lys Thr Ala Glu Arg Glu Gln Arg Ser Phe Cys Ser
            815                 820                 825

ACC GTG GCC GAT GAG ATC CGT TTC TCC CTT ACC TGC CAG CGT CGA GTC   2643
Thr Val Ala Asp Glu Ile Arg Phe Ser Leu Thr Cys Gln Arg Arg Val
830                 835                 840                 845

AAG CAC AAG CCT CAG CCT CCC ATG ATG GTC AAG ACT GAC GCC GTC ATC   2691
Lys His Lys Pro Gln Pro Pro Met Met Val Lys Thr Asp Ala Val Ile
                850                 855                 860

AAC ATG CAC ACA TTC AAT GAC CGC CGG CTT CCC GGC AAG GAC AGC ATG   2739
Asn Met His Thr Phe Asn Asp Arg Arg Leu Pro Gly Lys Asp Ser Met
            865                 870                 875

GCC TGC AGC ACA TCC TTA GCC CCT GTG TTC CCC TAGGCACAAC TGGGGTGGGG  2792
Ala Cys Ser Thr Ser Leu Ala Pro Val Phe Pro
            880                 885

ACCTCAGGCC TGGGGGCTGG GCAGAGGAAA GCAAAGGAGA TTGGAAGGAA CGTCCCCTGT  2852

ACCCGCACTG GGCTTGGGGA CCAGAGCTGC CACCTGCCTG TTGGGCCAGG AGCCTCCTGC  2912

CCTTACCTGC CAGGAAGCCA GCAGGCTCTC AGGCCAGCTG CTTGGGCTTC ATCCTCCTCA  2972

GATCTTCTGT GGGTTTCTAA AGCTGCCAGC CGAGATAGCC AAGGCCAAAG GAAGCACATG  3032

CCTCTCTCAG GCCAAACTCA CCTGCCCCTC AACTCTCCTC CAGAGTCAGA AGTTTCTGCC  3092

GCAGCCCTGC AGAGGGCACA GAAAATGGAA GACAGCTCTT ATATTGCCAT TTCTTCCACA  3152

AGAGCCCAGG CCTCCTACAG CTTGACCGTG AGGCCAGAGA CACAAGCCTT CGGCGCCTTA  3212
```

-continued

```
AGGATGTTCT AGCATGGCTG CCAATGGGAG CTCATGGTGA GGGATACCCA TCCCATATGC   3272

CTGGGCAGAA GGAAGACTTC ATCCCTCTGG GGCTGTTCAC GTGGTCCTAA TCTTCTGAAC   3332

TTGGCGCTGC CCCTGGCAGC CCCTGTTCTG GCAGAGTTGA AGACAGAGCT ACACAGGGGA   3392

AAAGAGGAGT TTGGGGTATG GGAGAGAAGA GAATGCACAA ACAGAGGCCG CCATTTTGGA   3452

TTCTTATGGA CAATGACCCA GTGGTTCCTA ATCCTCTAGG AGGTCTCTAA GAATATAAGT   3512

GGGGGAGTGG CCACAGAAAA TTCTTCTCCA CTTTCTAGCC AGAGGAGAGA GGACCCCCTG   3572

AATTTCTCAC AAAGGATGCC CAAAGATGCA GCCGGTATTT GGAATTC                 3619
```

(2) INFORMATION FOR SEQ ID NO:2:

(i) SEQUENCE CHARACTERISTICS:
        (A) LENGTH: 919 amino acids
        (B) TYPE: amino acid
        (D) TOPOLOGY: linear (ii) MOLECULE TYPE: protein (xi) SEQUENCE DESCRIPTION: SEQ ID NO:2:

```
Met Thr Ala Pro Trp Arg Arg Leu Arg Ser Leu Val Trp Glu Tyr Trp
-31 -30                 -25                 -20

Ala Gly Leu Leu Val Cys Ala Phe Trp Ile Pro Asp Ser Arg Gly Met
-15             -10                  -5                       1

Pro His Val Ile Arg Ile Gly Ile Phe Glu Tyr Ala Asp Gly Pro
             5                10                 15

Asn Ala Gln Val Met Asn Ala Glu His Ala Phe Arg Phe Ser Ala
         20                 25                 30

Asn Ile Ile Asn Arg Asn Arg Thr Leu Leu Pro Asn Thr Thr Leu Thr
     35                 40                 45

Tyr Asp Ile Gln Arg Ile His Phe His Asp Ser Phe Glu Ala Thr Lys
 50                 55                 60                     65

Lys Ala Cys Asp Gln Leu Ala Leu Gly Val Val Ala Ile Phe Gly Pro
                70                 75                 80

Ser Gln Gly Ser Cys Thr Asn Ala Val Gln Ser Ile Cys Asn Ala Leu
                85                 90                 95

Glu Val Pro His Ile Gln Leu Arg Trp Lys His His Pro Leu Asp Asn
            100                105                110

Lys Asp Thr Phe Tyr Val Asn Leu Tyr Pro Asp Tyr Ala Ser Leu Ser
115                 120                125

His Ala Ile Leu Asp Leu Val Gln Tyr Leu Lys Trp Arg Ser Ala Thr
130                 135                140                 145

Val Val Tyr Asp Asp Ser Thr Gly Leu Ile Arg Leu Gln Glu Leu Ile
                150                155                160

Met Ala Pro Ser Arg Tyr Asn Ile Arg Leu Lys Ile Arg Gln Leu Pro
                165                170                175

Ile Asp Ser Asp Asp Ser Arg Pro Leu Leu Lys Glu Met Lys Arg Gly
            180                185                190

Arg Glu Phe Arg Ile Ile Phe Asp Cys Ser His Thr Met Ala Ala Gln
        195                200                205

Ile Leu Lys Gln Ala Met Ala Met Gly Met Met Thr Glu Tyr Tyr His
210                 215                220                 225

Phe Ile Phe Thr Thr Leu Asp Leu Tyr Ala Leu Asp Leu Glu Pro Tyr
                230                235                240

Arg Tyr Ser Gly Val Asn Leu Thr Gly Phe Arg Ile Leu Asn Val Asp
            245                250                255
```

-continued

```
Asn Pro His Val Ser Ala Ile Val Glu Lys Trp Ser Met Glu Arg Leu
        260                 265                 270
Gln Ala Ala Pro Arg Ala Glu Ser Gly Leu Leu Asp Gly Val Met Met
        275                 280                 285
Thr Asp Ala Ala Leu Leu Tyr Asp Ala Val His Ile Val Ser Val Cys
290                 295                 300                 305
Tyr Gln Arg Ala Pro Gln Met Thr Val Asn Ser Leu Gln Cys His Gln
                310                 315                 320
His Lys Ala Trp Arg Phe Gly Arg Phe Met Asn Phe Ile Lys Glu
                325                 330                 335
Ala Gln Trp Glu Gly Leu Thr Gly Arg Ile Val Phe Asn Lys Thr Ser
        340                 345                 350
Gly Leu Arg Thr Asp Phe Asp Leu Asp Ile Ile Ser Leu Lys Glu Asp
        355                 360                 365
Gly Leu Glu Lys Val Gly Val Trp Ser Pro Ala Asp Gly Leu Asn Ile
370                 375                 380                 385
Thr Glu Val Ala Lys Gly Arg Gly Pro Asn Val Thr Asp Ser Leu Thr
                390                 395                 400
Asn Arg Ser Leu Ile Val Thr Thr Val Leu Glu Glu Pro Phe Val Met
                405                 410                 415
Phe Arg Lys Ser Asp Arg Thr Leu Tyr Gly Asn Asp Arg Phe Glu Gly
                420                 425                 430
Tyr Cys Ile Asp Leu Leu Lys Glu Leu Ala His Ile Leu Gly Phe Ser
        435                 440                 445
Tyr Glu Ile Arg Leu Val Glu Asp Gly Lys Tyr Gly Ala Gln Asp Asp
450                 455                 460                 465
Lys Gly Gln Trp Asn Gly Met Val Lys Glu Leu Ile Asp His Lys Ala
                470                 475                 480
Asp Leu Ala Val Ala Pro Leu Thr Ile Thr His Val Arg Glu Lys Ala
                485                 490                 495
Ile Asp Phe Ser Lys Pro Phe Met Thr Leu Gly Val Ser Ile Leu Tyr
        500                 505                 510
Arg Lys Pro Asn Gly Thr Asn Pro Ser Val Phe Ser Phe Leu Asn Pro
        515                 520                 525
Leu Ser Pro Asp Ile Trp Met Tyr Val Leu Leu Ala Tyr Leu Gly Val
530                 535                 540                 545
Ser Cys Val Leu Phe Val Ile Ala Arg Phe Ser Pro Tyr Glu Trp Tyr
                550                 555                 560
Asp Ala His Pro Cys Asn Pro Gly Ser Glu Val Val Glu Asn Asn Phe
                565                 570                 575
Thr Leu Leu Asn Ser Phe Trp Phe Gly Met Gly Ser Leu Met Gln Gln
        580                 585                 590
Gly Ser Val Leu Met Pro Lys Ala Leu Ser Thr Arg Ile Ile Gly Gly
        595                 600                 605
Ile Trp Trp Phe Phe Thr Leu Ile Ile Ile Ser Ser Tyr Thr Ala Asn
610                 615                 620                 625
Leu Ala Ala Phe Leu Thr Val Glu Arg Met Glu Ser Pro Ile Asp Ser
                630                 635                 640
Ala Asp Asp Leu Ala Lys Gln Thr Lys Ile Glu Tyr Gly Ala Val Lys
                645                 650                 655
Asp Gly Ala Thr Met Thr Phe Phe Lys Lys Ser Lys Ile Ser Thr Phe
                660                 665                 670
```

Glu Lys Met Trp Ala Phe Met Ser Arg Lys Pro Ser Ala Leu Val Lys
    675                 680                 685

Asn Asn Glu Glu Gly Ile Gln Arg Ala Leu Thr Ala Asp Tyr Ala Leu
690                 695                 700                 705

Leu Met Glu Ser Thr Thr Ile Glu Tyr Val Thr Gln Arg Asn Cys Asn
                710                 715                 720

Leu Thr Gln Ile Gly Gly Leu Ile Asp Ser Lys Gly Tyr Gly Ile Gly
            725                 730                 735

Thr Pro Met Gly Ser Pro Tyr Arg Asp Lys Ile Thr Ile Ala Ile Leu
            740                 745                 750

Gln Leu Gln Glu Glu Asp Lys Leu His Ile Met Lys Glu Lys Trp Trp
        755                 760                 765

Arg Gly Ser Gly Cys Pro Glu Glu Asn Lys Glu Ala Ser Ala Leu
770                 775                 780                 785

Gly Ile Gln Lys Ile Gly Gly Ile Phe Ile Val Leu Ala Ala Gly Leu
            790                 795                 800

Val Leu Ser Val Leu Val Ala Val Gly Glu Phe Val Tyr Lys Leu Arg
            805                 810                 815

Lys Thr Ala Glu Arg Glu Gln Arg Ser Phe Cys Ser Thr Val Ala Asp
    820                 825                 830

Glu Ile Arg Phe Ser Leu Thr Cys Gln Arg Arg Val Lys His Lys Pro
    835                 840                 845

Gln Pro Pro Met Met Val Lys Thr Asp Ala Val Ile Asn Met His Thr
850                 855                 860                 865

Phe Asn Asp Arg Arg Leu Pro Gly Lys Asp Ser Met Ala Cys Ser Thr
                870                 875                 880

Ser Leu Ala Pro Val Phe Pro
            885

(2) INFORMATION FOR SEQ ID NO:3:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

AACTCCCTGC AGTGCCATCA GCACAAGGCC TGGCGCTTTG GCGGCCGCTT           50

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

AACTCCCTGC AGTGCCATCG GCACAAGGCC TGGCGCTTTG GCGGCCGCTT           50

(2) INFORMATION FOR SEQ ID NO:5:

(i) SEQUENCE CHARACTERISTICS:
        (A) LENGTH: 100 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO:5:

AGAGAGAGAG CAGCGTTCCT TCTGCAGCAC CGTGGCCGAT GAGATCCGTT TCTCCCTTAC     60

CTGCCAGCGT CGAGTCAAGC ACAAGCCTCA GCCTCCCATG                           100

(2) INFORMATION FOR SEQ ID NO:6:

(i) SEQUENCE CHARACTERISTICS:
        (A) LENGTH: 100 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

AGAGAGAGAG CAGCGTTCCT TCTGCAGCAC CGTGGCCGAT GAGATCCGTT TCTCCCCACC     60

CTAAACGCAG CCGGCCTACC CCCTGCACAA GCAGGAATTC                           100

(2) INFORMATION FOR SEQ ID NO:7:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Leu Tyr Asp Ala Val His Ile Val Ser Val Cys Tyr Gln Arg Ala Pro
1               5                   10                  15

Gln Met Thr Val Asn Ser Leu Gln Cys His Gln His Lys Ala Trp Arg
            20                  25                  30

Phe Gly Gly Arg Phe Met Asn Phe Ile Lys Glu Ala Gln Trp Glu Gly
        35                  40                  45

Leu Thr
    50

(2) INFORMATION FOR SEQ ID NO:8:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (xi) SEQUENCE DESCRIPTION: SEQ ID NO:8:

Leu Tyr Asp Ala Val His Ile Val Ser Val Cys Tyr Gln Arg Ala Pro
1               5                   10                  15

Gln Met Thr Val Asn Ser Leu Gln Cys His Arg His Lys Ala Trp Arg
            20                  25                  30

Phe Gly Gly Arg Phe Met Asn Phe Ile Lys Glu Ala Gln Trp Glu Gly
        35                  40                  45

Leu Thr
    50

(2) INFORMATION FOR SEQ ID NO:9:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Ser Val Leu Val Ala Val Gly Glu Phe Val Tyr Lys Leu Arg Lys Thr
1               5                   10                  15

Ala Glu Arg Glu Gln Arg Ser Phe Cys Ser Thr Val Ala Asp Glu Ile
            20                  25                  30

Arg Phe Ser Leu Thr Cys Gln Arg Arg Val Lys His Lys Pro Gln Pro
        35                  40                  45

Pro Met
    50

(2) INFORMATION FOR SEQ ID NO:10:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ser Val Leu Val Ala Val Gly Glu Phe Val Tyr Lys Leu Arg Lys Thr
1               5                   10                  15

Ala Glu Arg Glu Gln Arg Ser Phe Cys Ser Thr Val Ala Asp Glu Ile
            20                  25                  30

Arg Phe Ser Pro Pro
        35

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATCGGCGGCA TCTTCATTGT TCTGGCTGCA GGACTCGTGC                              40

(2) INFORMATION FOR SEQ ID NO:12:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGGGTTTAAG CTTGCCGCCA CCATGACCGC TCCCTGGCGG CGCCTCCGGA GTCT             54

(2) INFORMATION FOR SEQ ID NO:13:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CAGGGCACTG GCCTCTTTGT                                                  20
```

We claim:

1. A method of assaying a test ligand for the ability to bind to a human CNS receptor, said method comprising the steps of
   (a) incubating a test ligand with: a genetically engineered cell that produces a kainate-binding human EAA5 receptor selected from the group consisting of:
   the human EAA5a receptor encoded by residues 1–888 of SEQ ID NO:2;
   the human EAA5b receptor encoded by residues 1–888 of SEQ ID NO:2 wherein residue 321 is arginine; and
   the human EAA5c receptor encoded by residues 1–838 of SEQ ID NO:2 followed by two proline residues;
   said cell having incorporated expressibly therein a heterologous DNA molecule encoding a human EAA5 receptor or, a membrane preparation derived from said cell, wherein said incubation is performed under conditions which permit binding of said test ligand with said human EAA5 receptor; and (b) determining the extent of binding between said test ligand and said human EAA5 receptor by comparison with kainate-binding to said EAA5 receptor.

2. The method of claim 1, wherein said cell is a mammalian cell.

3. The method of claim 2, wherein said test ligand is incubated with said membrane preparation derived from said human EAA5-producing cell.

* * * * *